United States Patent [19]

Sole

[11] Patent Number: 4,481,948

[45] Date of Patent: * Nov. 13, 1984

[54] MEDICAL INSTRUMENT, AND METHODS OF CONSTRUCTING AND UTILIZING SAME

[76] Inventor: Gary M. Sole, 3973 Nearbrook Dr., Bloomfield Hills, Mich. 48013

[*] Notice: The portion of the term of this patent subsequent to Jan. 11, 2000 has been disclaimed.

[21] Appl. No.: 394,409

[22] Filed: Jul. 1, 1982

Related U.S. Application Data

[63] Continuation-in-part of Ser. No. 221,065, Dec. 29, 1980, Pat. No. 4,367,744.

[51] Int. Cl.³ .............................................. A61B 17/39
[52] U.S. Cl. ............................ 128/303.14; 128/303.1; 219/236
[58] Field of Search ............ 128/303.1, 303.13, 303.14, 128/303.17; 219/227, 229, 233, 234, 236, 237, 238

[56] References Cited

U.S. PATENT DOCUMENTS

| | | | |
|---|---|---|---|
| 1,919,543 | 7/1933 | Doane | 128/303.17 |
| 2,033,397 | 3/1936 | Richman | 128/303.17 |
| 2,844,697 | 7/1958 | Emmerson | 219/233 X |
| 3,884,237 | 5/1975 | O'Malley | 128/303.14 |
| 4,108,181 | 8/1978 | Saliaris | 128/303.1 |

OTHER PUBLICATIONS

Reyman et al., "Experimental Intraocular Coagulation", Opthalmic Surgery, Jan.-Feb., 1972, vol. 3, No. 1, pp. 32-37.
Gorsch, "Biopsy in Proctology", American J. of Surgery, p. 484, Jun. 1936.

Primary Examiner—Lee S. Cohen
Attorney, Agent, or Firm—Irving M. Weiner; Pamela S. Burt; Anthony L. Cupoli

[57] ABSTRACT

A medical instrument including a cautery portion for use in performing an anterior or posterior capsulotomy during extracapsular cataract extraction surgery. A substantially rigid stem portion is connected between the cautery portion and a handle portion, and is provided with bends to facilitate maneuverability of the cautery portion and to avoid substantial interference with the surgical field of vision by the handle portion. An electrical path is defined through the handle portion and stem portion to the cautery portion so as to permit electrical current to be supplied to the cautery portion from an electrical apparatus which generates a radio frequency current. The cautery portion, as supplied with radio frequency current, becomes heated when in contact with an eye lens capsule so as to instantaneously and uniformly sear a peripheral extent of a portion of the lens capsule to be removed during surgery.

15 Claims, 13 Drawing Figures

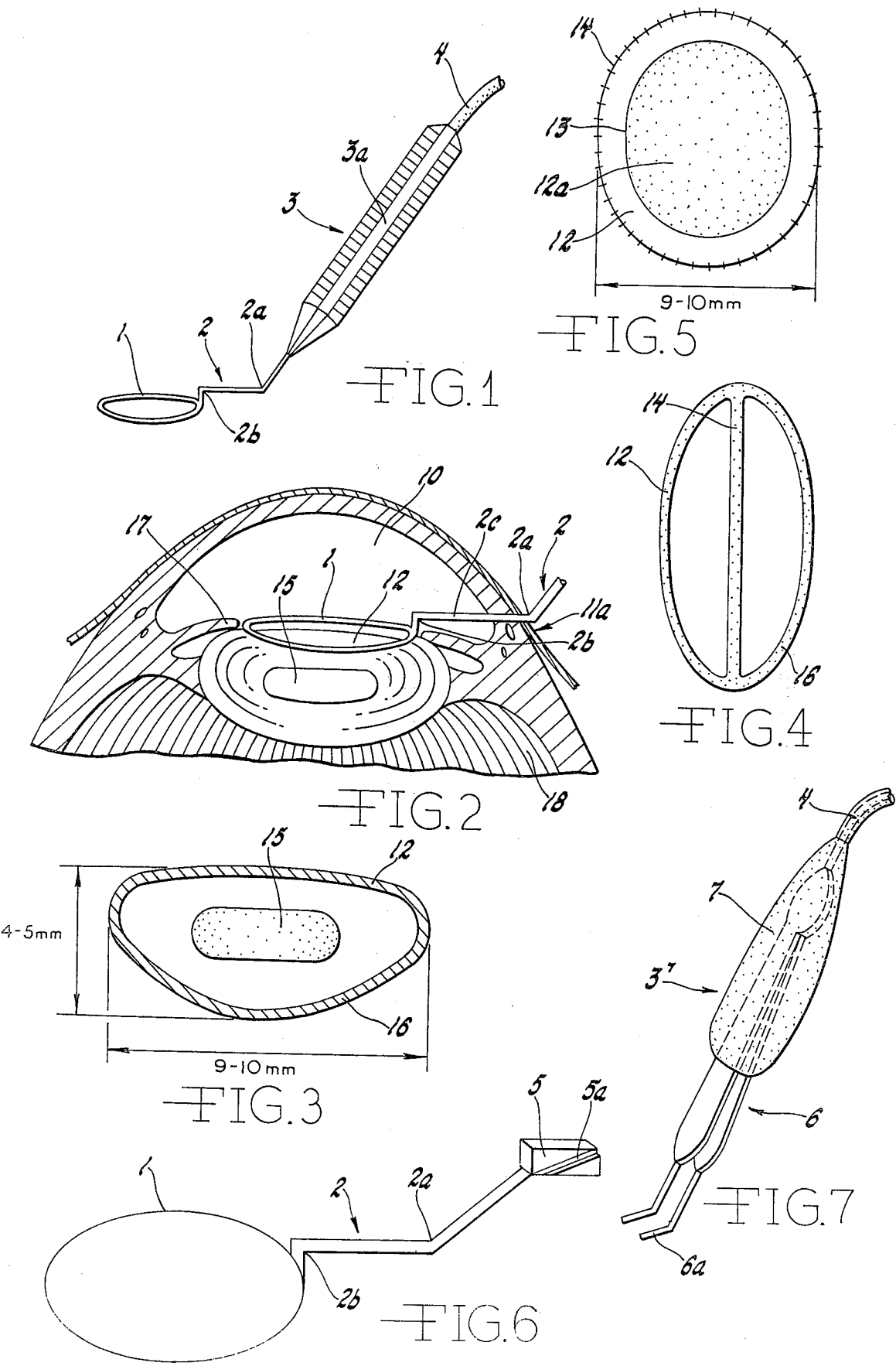

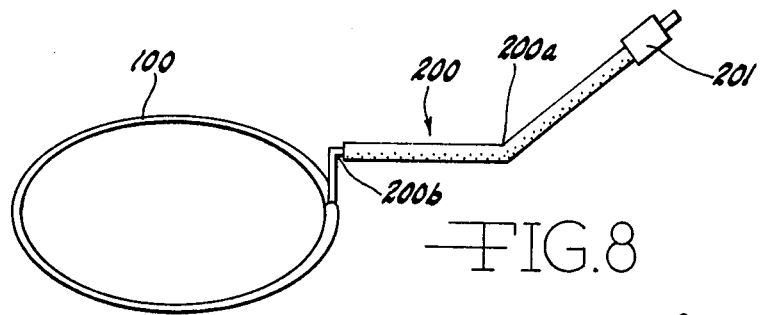
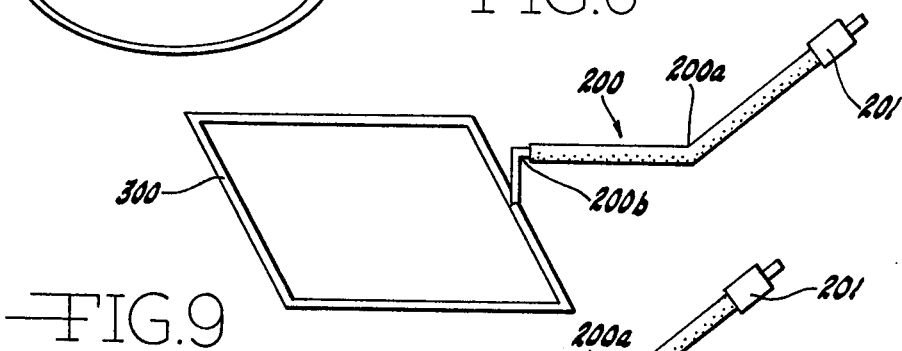
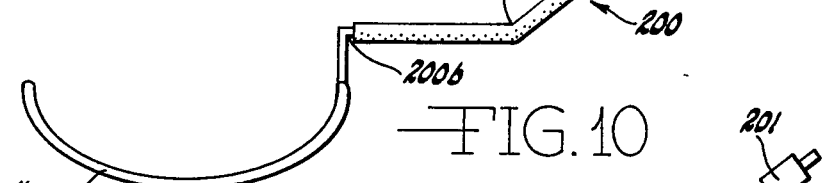
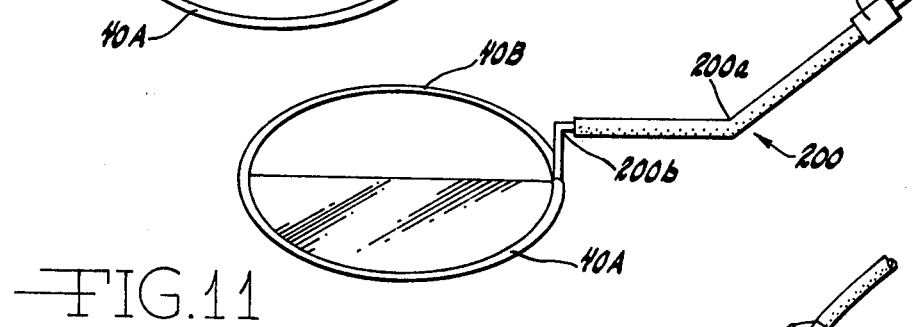
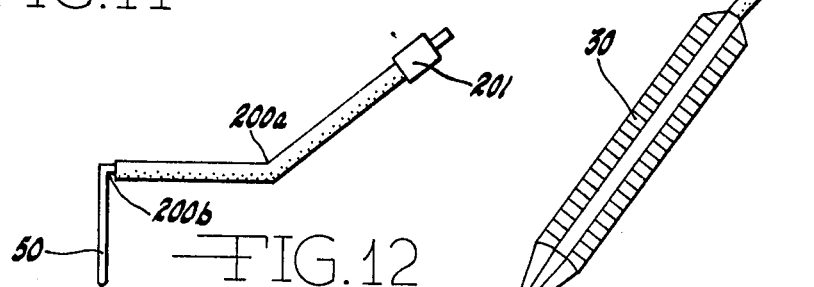
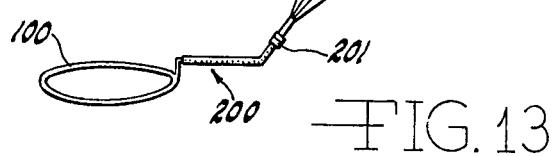

MEDICAL INSTRUMENT, AND METHODS OF CONSTRUCTING AND UTILIZING SAME

This is a continuation-in-part of application Ser. No. 221,065, filed Dec. 29, 1980, now U.S. Pat. No. 4,367,744.

BACKGROUND OF THE INVENTION

The present invention relates generally to a medical instrument for use in performing extracapsular cataract surgery, and a method for utilizing the medical instrument in performing such surgery.

More particularly, the invention relates to a medical instrument for use in performing an anterior and/or posterior capsulotomy during extracapsular cataract surgery. The medical instrument in accordance with the invention includes a wire cautery portion shaped to correspond to a desired peripheral extent of a portion of the capsule to be removed, such as an arcuate shape, for example. The cautery portion may be provided either in the form of an attachment for, or as an integral part of, an electrode of an electrosurgical apparatus of the type which generates a radio frequency (RF) current supply.

In performing a capsulotomy during extracapsular cataract surgery, the cautery portion is positioned in contact with the anterior (or posterior) lens capsule so as to sear the periphery of a portion of the lens capsule to be removed. The entire periphery of the lens capsule portion to be removed is seared in a consistently perfect manner either in a single searing action wherein the entire periphery is seared by a single contact of a first type of cautery portion with the surface of the capsule, or in a double searing manner wherein first one half peripheral extent and then the other is seared by twice contacting the surface of the capsule with a second type of cautery portion.

DESCRIPTION OF RELEVANT ART

The human eye includes a lens having the configuration of a biconvex disc. The lens surface comprises a capsule which includes an anterior capsule and a posterior capsule which meet at an equator. Zonules extending from the ciliary body are attached to the lens equator so as to secure the lens in position. Disposed within the lens capsule is a softer cortex and a firm inner nucleus.

In a healthy human eye, the lens is formed of a clear crystalline protein, however, the lens will at times opacify to form what is known as a cataract. When it is required to remove the cataract, the surgical procedure generally employed heretofore by operating surgeons is known as an intracapsular cataract extraction, wherein the cataract is removed within the lens capsule. Such procedure entails making a 180° incision at the superior limbus of the eye, retracting the iris, contacting the superior anterior lens capsule with an iceball (a cryoprobe), and extracting the entire lens within its capsule while separating same from the surrounding zonules.

In recent times, with the advent of implanted artificial intraocular lenses, the surgical microscope and phacoemulsification, many eye surgeons have come to prefer a surgical procedure known as extracapsular cataract extraction. In such procedure, the eye is opened at the superior limbus, and either hooks, scissors or special forceps are employed to open the anterior lens capsule and express from within the capsule the nucleus of the lens. Thereafter, the remaining cortical material is removed so as to thus leave a clear posterior lens capsule in the eye, which capsule provides a barrier between the anterior chamber and the vitreous cavity of the eye, as well as a resting surface for an implanted artificial lens.

One of the primary factors involved in attempting to successfully perform the extracapsular surgical method resides in successful removal of a large portion of the anterior lens capsule, i.e., a capsulotomy, which facilitates access to the lens nucleus and removal of the cortical material. Because any contact between the anterior and posterior lens capsules results in adherence together of the anterior and posterior capsules and resultant opacification of the posterior capsule, it is critical that any such contact between the capsules be avoided. However, the highly elastic nature of the lens capsule and the tendency of the edges thereof to roll and curl after the capsule has been cut renders such avoidance of capsule contact very difficult and greatly impairs the surgeon's chances of performing a perfect capsulotomy.

Performance of a posterior capsulotomy wherein the posterior capsule remaining in the eye after extracapsular surgery is itself incised is selective, depending upon the particular surgeon's preference. Such a technique may be employed to avoid the possibility of later opacification of the posterior capsule by performing the posterior capsulotomy in the final stages of the extracapsular cataract extraction procedure, such as after an intraocular lens has been implanted. Alternatively, a posterior capsulotomy may be deferred until any such time that the posterior lens capsule does in fact become opacified, and may then be performed on an outpatient basis, for example. In either event, the posterior capsulotomy, like the anterior capsulotomy, may be a difficult procedure to perform, particularly when the surgeon experiences difficulty in visually locating the posterior capsule within the eye.

Various methods have heretofore been employed for performing capsulotomies. In one such known method, a hooked needle (cystotome) is introduced into the eye at the limbus, and a 360° incision is made at the periphery of the anterior capsule. In other known methods, the anterior capsulotomy is performed with instruments such as scissors or special forceps. In the case of a posterior capsulotomy, such as after an intraocular lens has been implanted, the surgeon employs a hook to graze the posterior capsule and thereafter pulls on same to effect the incision.

The aforesaid known methods have attendant disadvantages due to the difficulties encountered in attempting to manipulate the aforesaid instruments within the very limited confines of the anterior segment of the eye while avoiding damage to the iris. Accordingly, and in view of the ever-increasing incidence of cataracts, there has developed a desideratum for a surgical instrument and technique for performing an anterior (or posterior) capsulotomy during extracapsular cataract surgery which overcomes the shortcomings and disadvantages attendant known instruments and techniques.

Some of the various attempts which have been made in the general field of cautery-type or heated-type medical instruments include: the "DENTAL INSTRUMENT" disclosed in U.S. Pat. No. 1,335,987 issued in 1920 to Reid et al; the "THERAPEUTIC APPLIANCE" disclosed in U.S. Pat. No. 1,615,828 issued in 1927 to Chesney; the "MEANS FOR EFFECTING THE BLOODLESS REMOVAL OF DISEASED TISSUE" disclosed in U.S. Pat. No. 1,919,543 issued in 1933 to Doane; the "METHOD OF AND APPARA- TUS FOR THE INTRACAPSULAR EXTRACTION OF THE CRYSTALLINE LENS OF AN EYE" disclosed in U.S. Pat. No. 2,033,397 issued in 1936 to Richman; the "APPARATUS FOR INTRAOCULAR SURGERY" disclosed in U.S. Pat. No. 3,884,237 issued in 1975 to O'Malley et al; the "CAUTERY DEVICE FOR OPHTHALMIC OR THE LIKE SURGICAL APPLICATION" disclosed in U.S. Pat. No. 4,108,181 issued in 1978 to Saliaris; the "DEVICE FOR REMOVING EXCRESCENCES AND POLYPS" disclosed in U.S. Pat. No. 4,202,338 issued in 1980 to Bitrolf; the "EXPERIMENTAL INTRAOCULAR COAGULATION" disclosed in article by Peyman et al appearing in *Opthalmic Surgery*, January-February 1972, Volume 3, No. 1, pp. 32–37; and the "BIOPSY IN PROCTOLOGY" disclosed in an article by Gorsch appearing in *American Journal of Surgery*, June 1936, p. 484. However, none of such known medical instruments and/or techniques provide any means for performing a consistently perfect capsulotomy during extracapsular cataract surgery as provided by the present invention by employing a very fine wire cautery portion to which an RF current is supplied to sear the periphery of a portion of an anterior (and/or posterior) capsule to be removed.

SUMMARY OF THE INVENTION

The present invention provides a medical instrument including cautery means for burning a lens capsule of an eye at the periphery of a portion of said capsule to be removed during surgery. The cautery means comprises a cautery portion formed of a fine wire and shaped so as to correspond to a peripheral extent of the portion of the capsule to be removed, and has a dimension corresponding to the diameter of the pupil of an eye to be operated upon. The instrument further includes a handle portion, and a substantially rigid elongated stem portion extending from the cautery portion and connected with the handle portion, the stem portion being electrically-conductive and covered with an electrically-insulative material along at least a portion of the length thereof. Means are provided for connecting the cautery portion, via the electrically-conductive stem portion, with an electrical apparatus which generates a radio frequency current supply; and the cautery portion, when supplied with the radio frequency current, is adapted to become heated when it is brought into contact with the peripheral extent of the portion of the capsule to be removed, whereby the peripheral extent of the capsule portion to be removed is seared by the cautery portion.

In a preferred embodiment, the cautery portion, when brought into contact with the peripheral extent of the portion of the capsule to be removed, becomes heated to effect a Bovie-like searing of the peripheral extent of the capsule portion.

The end portion of the stem adjacent the wire cautery portion is formed with a right angular bend, and in one embodiment the cautery portion is defined by a free first end of the stem portion extending from the right angular bend portion.

The other end portion of the stem may be removably secured to the handle portion in electrical contact with an electrical conductor extending through the handle portion, which conductor comprises the means for connecting the cautery portion with the electrical apparatus.

The cautery portion may have, for example, a substantially circular, rectangular or semicircular shape. In one embodiment wherein the cautery portion has a semicircular shape, the medical instrument comprises first and second cautery units and the semicircular cautery portion of one of the units is a mirror image of the semicircular cautery portion of the other unit. Such embodiment may be employed for effecting the aforesaid double-searing operation wherein first one half peripheral extent and then the other is seared by contacting the surface of the capsule with each of the mirror-image cautery portions individually, in succession.

The present invention further provides a method for utilizing the aforesaid medical instrument in performing extracapsular cataract surgery, and particularly for performing an anterior and/or a posterior capsulotomy. In accordance with such method, the pupil of an eye to be operated upon is dilated, and the wire cautery portion of the medical instrument is introduced into the eye. The cautery portion is positioned in contact with the surface of either the anterior or the posterior lens capsule, and the radio frequency current is applied from the electrical apparatus to the cautery portion so as to sear the lens capsule at the peripheral extent of the portion of the capsule to be removed.

It is an object of the present invention to provide a medical instrument including a wire cautery portion which can be readily manipulated by means of a bent stem portion connected with a handle portion, and which effects a clean, uniform searing of the lens capsule by means of radio frequency current to ensure successful performance of a capsulotomy during extracapsular cataract surgery.

The above and other objects, details and advantages of the present invention will become apparent from the following detailed description, when read in conjunction with the accompanying drawings.

BRIEF DESCRIPTION OF THE DRAWINGS

FIG. 1 is a perspective view of a medical instrument in accordance with a first embodiment of the invention.

FIG. 2 is a sectioned side view of a human eye during a surgical procedure employing the medical instrument in accordance with the invention.

FIG. 3 is a sectioned side view of a lens of a human eye.

FIG. 4 is a side view of a lens capsule of a human eye.

FIG. 5 is a top plan view of an anterior lens capsule showing a portion thereof to be removed during a capsulotomy.

FIG. 6 is a perspective view of a wire cautery portion with attached stem and connecting portions of a medical instrument in accordance with a second embodiment of the invention.

FIG. 7 is a perspective view of a handle portion for connection with the connecting portion of FIG. 6 in accordance with the second embodiment of the invention.

FIG. 8 is a perspective view of a wire cautery portion with attached stem in accordance with a third embodiment of the invention.

FIG. 9 is a perspective view of a wire cautery portion with attached stem in accordance with a fourth embodiment of the invention.

FIG. 10 is a perspective view of a wire cautery portion with attached stem in accordance with a fifth embodiment of the invention.

FIG. 11 is a perspective view of the wire cautery portion according to the fifth embodiment, illustrating the mirror image relation of a pair of cautery units.

FIG. 12 is a perspective view of a medical instrument in accordance with a sixth embodiment of the invention.

FIG. 13 is a perspective view showing the wire cautery portion with attached stem of FIG. 8, as connected with a handle portion.

DETAILED DESCRIPTION OF PREFERRED EMBODIMENTS

With reference to FIGS. 1–7, there are shown medical instruments in accordance with first and second embodiments of the invention as disclosed in my aforesaid application Ser. No. 221,065 filed Dec. 29, 1980.

As shown in FIG. 1, the medical instrument in accordance with a first embodiment of the present invention includes a cautery portion 1, an elongated stem portion 2 interconnected at a first end thereof with the cautery portion 1 and at a second end thereof with a handle portion 3, and an electrical conductor 4 connected to the upper end of handle portion 3.

The handle 3 is substantially elongated and may have a generally cylindrical shape, or any other desired suitable shape. Handle 3 is fabricated of an electrically-insulative material such as plastic or the like, and is provided with an electrical conductor or wire 3a extending therethrough. The electrical conductor 4 attached to the upper end of handle 3 may comprise an extension of conductor 3a or alternatively may comprise a separate wire electrically connected with conductor 3a, and is covered with an electrically-insulative material. If desired, conductor 4 may be removably attached to the upper end of handle 3 by suitable connecting means. Conductor 4 is provided at the free end thereof with a suitable plug (not shown) for connection with an electrical power source (not shown).

The elongated stem portion 2 may have the second end thereof either fixedly secured to the lower end of handle 3, or removably secured thereto by suitable connecting means. In this regard it will be understood that by removably securing stem portion 2 to handle 3, the combined stem and cautery portions of the instrument may be considered as a disposable unit. Alternatively, if desired, the entire instrument may be provided in a disposable form.

Stem portion 2 is substantially rigid, and is fabricated of an electrically conductive material such as a length of wire, covered along the length thereof with an electrically-insulative material, with the outside diameter of stem portion 2 being as small as possible. The second end of stem portion 2 connected to handle 3 is in electrical contact with conductor 3a of handle 3, such that an electrically-conductive path is defined from conductor 4, through handle 3 (via conductor 3a), and through stem portion 2 to the first end thereof secured to cautery portion 1. The stem portion 2 is provided with an obtuse angular bend 2a in an intermediate portion thereof, which is bent at an angle of approximately 120°, for example. At the first end portion thereof adjacent cautery portion 1, stem portion 2 is provided with a substantially right angular bend 2b. Such bend portions 2a and 2b are provided in order to minimize interference with the surgical field of vision, particularly by handle portion 3, and to facilitate manipulation of cautery portion 1 when the medical instrument is being employed for use during surgery.

The wire cautery portion 1 is integrally connected with the first end of stem portion 2 in electrical contact therewith, and is formed of a substantially rigid or shape-retentive wire which is as fine as possible while still being capable of reaching a suitable temperature for burning the anterior lens capsule of an eye in the presence of aqueous material, such temperature being in the range of, for example, 500° to 2000° C. The cautery portion 1 has a substantially circular shape, or may be formed to have other shapes as desired by the surgeon. The overall diameter of cautery portion 1 is dependent upon the diameter of the pupil of the particular eye upon which surgery is to be performed, and the present invention thus contemplates providing medical instruments according to the invention with cautery portions 1 of varying diameters. Preferably, the medical instruments would be provided with cautery portions 1 having varying diameters of from 6 mm to 9 mm provided in 0.5 mm increasing incremental sizes to provide the surgeon with a desirable selection of cautery portion sizes. In this regard, the stem portion 2 for the cautery portion 1 will have a length dimension dependent upon the diameter size of the cautery portion, as will be described in greater detail hereinbelow.

A surgical technique utilizing the medical instrument as thus far described in performing extracapsular cataract surgery, and particularly in performing a capsulotomy during extracapsular cataract surgery, will now be described hereinbelow with reference to FIGS. 2–5.

In FIG. 2, the cautery portion 1 is shown as introduced into the anterior chamber 10 of the eye at the limbus portion 11a of the cornea. The pupil of the eye is maximally dilated to permit positioning of cautery portion 1 in contact with the surface of the anterior lens capsule 12 without contacting other ocular structure. With cautery portion 1 thus positioned in contact with the surface of anterior lens capsule 12 as shown in FIG. 2, electrical current is then applied to cautery portion 1 via conductor 4, conductor 3a, and electrically-conductive stem portion 2. The very fine wire cautery portion 1 is rapidly heated by such applied current for an instant so as to burn a clean, substantially perfect and uniform circle 13 in the anterior capsule 12, as shown in FIG. 5. It will thus be understood that the medical instrument in accordance with the invention functions in a manner analogous to a conventional branding iron, although much more delicately, in burning the circle 13 in anterior lens capsule 12. After the circle 13 has been burned in the anterior lens capsule 12 by means of cautery portion 1, the surgeon then removes portion 12a (FIG. 5) of anterior lens capsule 12 within circle 13, i.e., by washing it out. Thereafter, the extracapsular cataract surgery is continued (with the use of forceps and/or other suitable instruments) by expressing from within the lens capsule the nucleus 15 of the lens (FIGS. 2 and 3) and removing the remaining cortical material so as to leave only a clear posterior lens capsule 16 (FIGS. 2–4) within the eye to serve as a barrier between the anterior chamber and the vitreous cavity.

The medical instrument as described hereinabove should be fabricated so as to be very light in overall construction, so as to avoid excessive posterior pressure on the lens during the anterior capsulotomy. Further, consideration should be given to the overall construction and the material forming the various component portions of the instrument to ensure that the wire cautery portion 1 will reach its burning temperature as rapidly as possible, maintain such temperature only long enough to burn the circle 13, and then rapidly cool. In this regard, it will be understood that any suitable switches and/or other electrical circuitry components may be employed to effect the aforesaid rapid heating and cooling characteristics.

Because the electrically-conductive stem portion 2 is covered with an electrically-insulative material as described hereinabove, it will be understood that inadvertent burning of the iris 17, cornea 11 or sclera 18 (FIG. 2) by such stem portion 2 will be effectively avoided. With further regard to stem portion 2, the dimension thereof in the straight portion 2c between bends 2a and 2b is determined such that the obtuse angular bend 2a will be located just outside of the cornea 11 during the capsulotomy, as shown in FIG. 2, to thus facilitate manipulation and positioning of the cautery portion 1 within the anterior chamber 10. Accordingly, it will be understood that such dimension of stem portion 2c will be determined in accordance with the overall diameter of cautery portion 1, with longer lengths thereof being required with cautery portions of smaller diameters. By way of example, for a 9 mm diameter cautery portion 1, a suitable length for stem portion 2c would be approximately 4 mm.

With reference to FIGS. 4 and 5, designated at 14 are the zonular attachments disposed at the equator at which the anterior and posterior lens capsules meet, and attaching from the ciliary body so as to secure the lens in position.

In accordance with a second embodiment of the invention as shown in FIGS. 6 and 7, the first end of stem portion 2 is connected with cautery portion 1 as described hereinabove in connection with the first embodiment of the invention, however, the second end of stem portion 2 is secured to an intermediate connecting portion 5. Connecting portion 5 is formed of an electrically-insulative material and is shown in FIG. 6 as having a box shape, however, it will be understood that connecting portion 5 may have any desired shape. A pair of receiving portions or grooves 5a are provided in connecting portion 5 and have electrical contact points provided therein and electrically connected with the inner electrically-conductive portion (wire) of stem portion 2. If desired, connecting portion 5 may be connected with a suitable electrical conductor for direct connection to an electrical power source (not shown).

With reference to FIG. 7, there is shown a handle portion 3' in accordance with the second embodiment of the invention. Handle portion 3' is constructed mainly of McPherson Forceps 6 which may be connected via electrical conductor 4 to an electrical power source (not shown). A covering 7 of electrically-insulative material is disposed over the forceps 6 to define a hand grip portion, with the lower operating tips 6a of the forceps extending therefrom. The tips 6a may be inserted within the receiving portions 5a of connecting portion 5 (FIG. 6), and the receiving portions 5a are particularly adapted in size and shape to securely respectively receive operating tips 6a therein. Upon insertion of tips 6a within receiving portions 5, an electrical path will be established from conductor 4, through forceps 6, through the contacts in portions 5a, and through stem portion 2 to cautery portion 1. When desired, the tips 6a of forceps 6 may be slidably removed from receiving portions 5a, and thereafter employed separately as a surgical instrument. It will thus be understood that the medical instrument in accordance with the second embodiment of the invention provides a dual-instrument capacity, and if desired the portion of the instrument shown in FIG. 6 including cautery portion 1 may be disposed with after use.

With reference now to FIGS. 8-13, the third through sixth embodiments of the invention will now be described hereinbelow, each of which embodiments relates to a medical instrument supplied with RF current rather than the conventional electrical current employed in the preceding first and second embodiments of the invention.

In each of the third through sixth embodiments of the invention, the medical instrument is supplied with power from an electrical apparatus which generates a radio frequency current supply, i.e., having a frequency higher than 10,000 hertz. Such an apparatus might comprise, by way of example, an electrosurgical generator of a known type which is commonly employed in performing electrosurgical procedures in various fields of surgical specialty. One known electrosurgical generator suitable for use in supplying power to the medical instrument in accordance with the invention is manufactured by Davol Inc. of Cranston, R.I., and is capable of producing a Bovie-like fulguration surgical effect as well as having both monopolar and bipolar capabilities.

One of the primary advantages afforded by employing RF current in the following embodiments of the invention resides in the fact that the cautery portion will become heated only when it is brought into contact with the peripheral extent of the portion of the lens capsule to be removed, to thus effect the desired searing action without being heated previous thereto. In addition, whereas the medical instruments described with respect to the preceding embodiments of the invention require a completed electrical circuit passing through the wire cautery portion, those embodiments described hereinbelow for use with RF current are not subject to such requirement. Accordingly, it will be understood that the fine wire from which the cautery portions are formed in accordance with each of the following embodiments of the invention may advantageously be even finer than that employed in the preceding embodiments.

In the third embodiment of the invention shown in FIG. 8, the cautery portion 100 is substantially similar to cautery portion 1 described hereinabove in connection with the first embodiment of the invention, although it is formed of a finer wire as described above, and has a substantially circular shape corresponding to a circular peripheral extent of a portion of a lens capsule to be removed. As in the first embodiment of the invention, it is contemplated that cautery portion 100 may be provided in varying diameters of from 6 mm to 9 mm provided in 0.5 mm increasing incremental sizes so as to provide the surgeon with a desirable selection of cautery portion sizes corresponding to pupils of varying diameters.

The stem portion 200 shown in FIG. 8 is also substantially similar to stem portion 2 described in connection with the first embodiment of the invention, and includes an obtuse angular bend 200a (e.g., approximately 120°) in an intermediate portion thereof, and a substantially right angular bend 200b adjacent the first end portion thereof which is integrally connected with cautery portion 100. Stem portion 200 comprises a substantially rigid length of electrically conductive material having a length dimension dependent upon the diameter size of cautery portion 100, similar to the first embodiment of the invention, and is covered with an electrically-insulative material substantially along the length thereof.

The stem portion 200 includes a second end 201 in the form of a connecting portion adapted to be connected with an electrode of an electrical apparatus which generates RF current (described hereinabove). A handle portion 30 formed of an electrically-insulative material with an electrical conductor extending therethrough (i.e., similar to handle 3 in the first embodiment) may be provided either integrally with such electrode of the electrical apparatus for connection with end 201 as shown in FIG. 13, or may extend integrally from stem portion 200 for connection with the electrode of the electrical apparatus.

It will thus be understood that the medical instrument shown in FIG. 8 comprises an attachment for the aforesaid electrical apparatus which generates an RF current supply, and is substantially similar in other respects to the first embodiment of the invention.

With reference to FIG. 9, the medical instrument in accordance with the fourth embodiment of the invention is substantially the same as the third embodiment shown in FIG. 8, except that the cautery portion 300 of this embodiment is substantially rectangular in shape, i.e., corresponding to a rectangular peripheral extent of a portion of a lens capsule to be removed.

A surgical technique utilizing the medical instrument in accordance with the third and fourth embodiments of the invention in performing extracapsular cataract surgery, and particularly in performing an anterior capsulotomy during extracapsular cataract surgery, is described hereinbelow.

The cautery portion 100 (or 300) is introduced into the anterior chamber 10 of the eye at the limbus portion 11a of the cornea, in the same manner as cautery portion 1 shown in FIG. 2. The pupil of the eye is maximally dilated to permit positioning of the cautery portion in contact with the surface of the anterior lens capsule 12 without contacting other ocular structure. Preferably, air is injected into anterior chamber 10 (after the eye has been opened), so as to push out the normal fluids within the chamber and thereby increase the surgeon's visibility of the occular structure as well as avoid any possibility of a cooling effect on the cautery portion which might occur due to the normal fluids.

With the cautery portion 100 (or 300) thus positioned in contact with the surface of anterior lens capsule 12 (similar to FIG. 2), radio frequency current is applied to cautery portion 100 (or 300) through handle 30 and electrically-conductive stem portion 200. The very fine wire cautery portion 100, as positioned against the surface of the anterior lens capsule, is very expeditiously heated for an instant so as to sear a clean, substantially perfect and uniform circle 13 (FIG. 5) in the anterior capsule (although it will be understood that a clean and perfectly uniform rectangle would be attained when alternatively using cautery portion 300). The peripheral extent of the desired portion of capsule to be removed is thus instantaneously and perfectly uniformly seared by the cautery portion, as supplied with radio frequency current to effect a Bovie-like searing effect.

After the circle (or rectangle) has been burned in the anterior lens capsule as described above, the surgeon then removes the seared-off portion (i.e., portion 12a in FIG. 5), such as by washing it out. Thereafter, the extracapsular cataract surgery is continued (with the use of forceps and/or other suitable instruments) by expressing from within the lens capsule the nucleus 15 of the lens (FIGS. 2 and 3) and removing the remaining cortical material so as to leave only a clear posterior lens capsule 16 (FIGS. 2-4) within the eye to serve as a barrier between the anterior chamber and the vitreous cavity, as well as to provide a resting place for any artificial intraocular lens to be implanted.

The above-described searing action, effected by means of radio-frequency current supplied to the cautery portion, provides an instantaneous, accurate and effective searing of the periphery of the lens capsule portion to be removed. Desirably, the aforesaid electrical apparatus which generates the RF current is provided with a conveniently operated actuating member, such as a foot pedal, to be operated by the surgeon when the cautery portion has been properly positioned in contact with the anterior lens capsule. It will also be understood that normally an electrical grounding device is employed (such as by being positioned under the patient) in conjunction with electrosurgical procedures involving radio frequency current. Further, as mentioned previously, the cautery portion will become heated by the RF current supplied thereto only when it is in contact with the resistance offered by the anterior lens capsule tissue, thus avoiding any undesirable heating of the cautery portion prior to its proper positioning.

The dimension of stem portion 200 in the straight portion between bends 200a and 200b, similar to that of stem portion 2 of the first embodiment, is determined such that the obtuse angular bend 200a will be located just outside of the cornea 11 during the capsulotomy (FIG. 2), to thus facilitate manipulation and positioning of the cautery portion within the anterior chamber 10. Accordingly, it will be understood that such dimension of the stem portion will be determined in accordance with the overall diameter (or other applicable dimension) of the cautery portion, with longer lengths thereof being required with cautery portions of smaller diameters. By way of example, for a 9 mm diameter cautery portion 100, a suitable length for such part of stem portion 200 would be approximately 4 mm.

With reference to FIGS. 10 and 11, there is shown a medical instrument in accordance with a fifth embodiment of the invention. In this embodiment, the medical instrument comprises first and second cautery units, with the stem portion 200 of each of such units being substantially the same as that described in connection with the foregoing embodiments. The first of such cautery units, shown in FIG. 10, is provided with a cautery portion 40A formed of the same fine shape-retentive wire employed for cautery portions 100 and 300 and having a substantially semicircular shape. The second of such cautery units (FIG. 11) has an identical construction to the first unit, except that the cautery portion 40B thereof is a mirror-image of cautery portion 40A of the first unit. Each of the cautery units, by virtue of the semicircular configuration of the cautery portions thereof, may preferably by monopolar.

The pair of cautery units including cautery portions 40A and 40B are employed for surgery in much the same manner as described hereinabove in connection with the third and fourth embodiments of the invention, except that in this case a double-searing operation is effected. The first cautery unit including portion 40A, for example, is first employed in the foregoing manner to effect the desired searing action by means of radio frequency current supplied to the cautery portion, with only one-half of the desired circular periphery of the lens portion to be removed being seared by cautery portion 40A. Thereafter, the surgeon employs the second unit, including cautery portion 40B, to effect instantaneous searing of the opposite one-half of the circular periphery of the lens portion to be removed, thus completing the desired circular burn.

In FIG. 12, there is shown a medical instrument according to a sixth embodiment of the invention wherein the cautery portion 50 is defined by an extended free first end (i.e., extending from right-angular bend portion 200b) of stem portion 200. Such instrument can be employed when it is desired to sear only one particular point of the lens capsule tissue at a given time.

When it is desired to perform a posterior capsulotomy, either in the final stages of an extracapsular cataract extraction procedure (such as after an intraocular lens has been implanted) or in a later operation, the surgeon may employ the medical instrument shown in FIG. 12. The single point configuration of cautery portion 50 of such embodiment may be readily employed in a posterior capsulotomy to effect the same radio frequency searing action as described hereinabove in connection with anterior capsulotomies. Such medical instrument shown in FIG. 12 may also be employed in performing anterior capsulotomies, as desired.

Although there have been described what are at present considered to be the preferred embodiments of the invention, it will be understood that the invention may be embodied in other specific forms without departing from the spirit or essential characteristics thereof. The present embodiments are therefore to be considered in all respects as illustrative, and not restrictive. The scope of the invention is indicated by the appended claims rather than by the foregoing description.

I claim:

1. A medical instrument, comprising:
   cautery means for burning a lens capsule of an eye at the periphery of a portion of said capsule to be removed during surgery;
   said cautery means comprising a cautery portion formed of a fine wire and shaped so as to correspond to a peripheral extent of said portion of said capsule to be removed;
   a handle portion;
   a substantially rigid elongated stem portion extending from said cautery portion and connected with said handle portion, said stem portion being electrically-conductive and covered with an electrically-insulative material;
   said cautery portion having a dimension corresponding to the diameter of the pupil of an eye to be operated upon;
   means for connecting said cautery portion, via said electrically-conductive stem portion, with an electrical apparatus which generates a radio frequency current supply; and
   said cautery portion, when supplied with said radio frequency current, being adapted to become heated when said cautery portion is brought into contact with said peripheral extent of said portion of said capsule to be removed, whereby said peripheral extent of said capsule portion to be removed is seared by said cautery portion.

2. A medical instrument according to claim 1, wherein:
   said stem portion comprises a wire covered with said electrically-insulative material along at least a portion of the length thereof; and said stem portion is formed with an obtuse angular bend in an intermediate portion thereof between said cautery portion and said handle portion.

3. A medical instrument according to claim 2, wherein:
   said stem portion is formed with a right angular bend in a first end portion thereof adjacent said wire cautery portion.

4. A medical instrument according to claim 2, wherein:
   the length of said stem portion from a first end portion adjacent said wire cautery portion to said obtuse angular bend is substantially equal to or greater than 4 mm.

5. A medical instrument according to claim 1, wherein:
   said means for connecting said cautery portion with said electrical apparatus includes an electrical conductor extending through said handle portion and connected with said electrically-conductive stem portion; and
   said handle portion is fabricated of an electrically-insulative material surrounding said electrical conductor.

6. A medical instrument according to claim 5, wherein:
   one end portion of said stem portion is removably secured to said handle portion in electrical contact with said electrical conductor.

7. A medical instrument according to claim 6, wherein:
   said stem portion is formed with a right angular bend in another end portion thereof; and
   said cautery portion extends from said right angular bend in said stem portion.

8. A medical instrument according to claim 1, wherein:
   said stem portion is formed with a right angular bend in a first end portion thereof; and
   said cautery portion extends from said right angular bend in said first end portion of said stem portion.

9. A medical instrument according to claim 1, wherein
   said cautery portion has a substantially circular shape.

10. A medical instrument according to claim 1, wherein:
    said cautery portion has a substantially semicircular shape.

11. A medical instrument according to claim 1, wherein:
    said cautery portion has a substantially rectangular shape.

12. A medical instrument kit, comprising:
    a medical instrument including cautery means for burning a lens capsule of an eye at the periphery of a portion of said capsule to be removed during surgery;
    said cautery means comprising a cautery portion formed of a fine wire and shaped so as to correspond to a peripheral extent of said portion of said capsule to be removed;
    a handle portion;
    a substantial rigid elongated stem portion extending from said cautery portion and connected with said handle portion, said stem portion being electrically-conductive and covered with an electrically-insulative material;

said cautery portion having a dimension corresponding to the diameter of the pupil of an eye to be operated upon;

means for connecting said cautery portion, via said electrically-conductive stem portion, with an electrical apparatus which generates a radio frequency current supply;

said cautery portion, when supplied with said radio frequency current, being adapted to become heated when said cautery portion is brought into contact with said peripheral extent of said portion of said capsule to be removed, whereby said peripheral extent of said capsule portion to be removed is seared by said cautery portion;

said cautery portion has a substantially semicircular shape;

first and second cautery units each comprising said cautery means and said stem portion; and said semicircular cautery portion of said first cautery unit is substantially a mirror image of said semicircular cautery portion of said second cautery unit.

13. A method for utilizing a medical instrument in performing extracapsular cataract surgery, comprising the steps of:

dilating a pupil of an eye to be operated upon;
introducing a cautery portion of said medical instrument into said eye;
positioning said cautery portion in contact with a surface of an anterior or posterior lens capsule of said eye; and
applying radio frequency current to said cautery portion so as to sear said lens capsule at a peripheral extent of a portion of said lens capsule to be removed during said extracapsular cataract surgery.

14. A method according to claim 13, wherein:
said cautery portion is positioned in contact with the surface of a posterior lens capsule of said eye; and
said method further comprises the step of moving said cautery portion so as to sear a slit in said posterior lens capsule.

15. A method according to claim 13, further comprising the step of:
injecting air into the anterior chamber of said eye.

* * * * *